(12) United States Patent  
Zreiqat et al.

(10) Patent No.: US 9,005,647 B2  
(45) Date of Patent: Apr. 14, 2015

(54) BIOCOMPATIBLE MATERIAL AND USES THEREOF

(75) Inventors: Hala Zreiqat, Chatswood (AU); Chengtie Wu, Carlton (AU); Yogambha Ramaswamy, Kingsford (AU)

(73) Assignee: The University of Sydney, New South Wales (AU)

( * ) Notice: Subject to any disclaimer, the term of this patent is extended or adjusted under 35 U.S.C. 154(b) by 24 days.

(21) Appl. No.: 12/739,611

(22) PCT Filed: Oct. 24, 2008

(86) PCT No.: PCT/AU2008/001582
§ 371 (c)(1),
(2), (4) Date: Apr. 23, 2010

(87) PCT Pub. No.: WO2009/052583
PCT Pub. Date: Apr. 30, 2009

(65) Prior Publication Data
US 2010/0324677 A1    Dec. 23, 2010

(30) Foreign Application Priority Data

Oct. 24, 2007  (AU) ............................... 2007905843

(51) Int. Cl.
*A61F 2/28* (2006.01)
*A61F 2/02* (2006.01)
*C04B 35/00* (2006.01)
*C04B 35/16* (2006.01)
*A61L 27/10* (2006.01)
*A61L 27/30* (2006.01)
(Continued)

(52) U.S. Cl.
CPC ............... *A61L 27/10* (2013.01); *A61L 27/306* (2013.01); *A61L 2430/02* (2013.01); *C01B 33/20* (2013.01); *C04B 35/22* (2013.01); *C04B 2235/3232* (2013.01); *C04B 2235/6562* (2013.01)

(58) Field of Classification Search
None
See application file for complete search history.

(56) References Cited

U.S. PATENT DOCUMENTS

2004/0023784 A1   2/2004  Yu et al.
2004/0258732 A1*  12/2004  Shikinami .................... 424/426
(Continued)

OTHER PUBLICATIONS

John W. Anthony, Richard A. Bideaux, Kenneth W. Bladh, and Monte C. Nichols, Eds., Handbook of Mineralogy, Mineralogical Society of America, Chantilly, VA 20151-1110, USA. http://www.handbookofmineralogy.org.*

(Continued)

*Primary Examiner* — Ileana Popa
*Assistant Examiner* — Nicole Babson
(74) *Attorney, Agent, or Firm* — Nixon Peabody LLP; Jeffrey L. Costellia

(57) ABSTRACT

The present invention relates to a biocompatible ceramic material comprising Baghdadite ($Ca_3ZrSi_2O_9$), and a method for its preparation. Preferably the Baghdadite is synthetically prepared. The present invention also relates to an implantable medical device comprising biocompatible Baghdadite, and a method for its production. The present invention further relates to a method for improving the long term stability of an implantable medical device and an implantable drug delivery device comprising Baghdadite. Further, the present invention relates to the use of comprising biocompatible Baghdadite in the regeneration or resurfacing of tissue.

21 Claims, 11 Drawing Sheets
(4 of 11 Drawing Sheet(s) Filed in Color)

(51) Int. Cl.
  *C01B 33/20* (2006.01)
  *C04B 35/22* (2006.01)
  *B05D 7/00* (2006.01)

(56) References Cited

U.S. PATENT DOCUMENTS

2007/0098811 A1* 5/2007 Lu et al. .................. 424/602
2007/0128245 A1* 6/2007 Rosenberg et al. ........... 424/423

OTHER PUBLICATIONS

Hulbert, The Use of Alumina and Zirconia in Surgical Implants, An Introduction to Bioceramics, 1993, pp. 25-40.*
Al-Hermezi, et al., "Baghdadite, A New Calcium Zirconium Silicate Mineral From Iraq", Mineralogical Magazine, Mar. 1986, vol. 50, pp. 119-123.
Plaisier, et al., "Structure Determination of $Ca_3HfSi_2O_9$ and $Ca_3ZrSi_2O_9$ from Powder Diffraction", Journal of Solid State Chemistry, 1995, vol. 115, pp. 464-468.
Sidike, et al., "Yellow Fluorescence from Baghdadite and Synthetic $Ca_3(Zr,TI)Si_2O_9$", Phys Chem Minerals, 2006, vol. 32, pp. 665-669.
Ramaswamy, et al., "The Responses of Osteoblaste, Osteoclasts and Endothelial Cells to Zirconium Modified Calcium-Silicate-Based Ceramic", Biomaterials, 2008, vol. 29, pp. 4392-4402.
International Search Report for PCT/AU2008/001582 dated Dec. 11, 2008.
International Preliminary Report of Patentability for PCT/AU2008/001582 dated Apr. 2, 2009.
Search Report—Supplementary European Search Report mailed Dec. 12, 2012.
Database CA (Online)—Chemical Abstracts Service, Columbus, Ohio, US; J. Iwanciw; "Some Aspects of Semi-Quantitative and Quantitative Determination of Synthetic Compounds of Ca)-$SiO_2$—$ZrO_2$ System". XP002688577, retrieved from STN-International accession No. 123-294345, *abstract* & Applied Crystallography, vol. 1995, No. 16th, 1994, pp. 363-366.
Blasse et al.; "Yellow Zirconate Luminescence in $Ca_3ZrSi_2O_9$"; *Journal of Alloys and Compounds*, vol. 217, 1995, pp. 29-30.
Weichang Xue et al.: "In Vivo Evaluation of Plasma-Sprayed Wolastonite Coating". *Biomaterials*, vol. 26, 2005, pp. 3455-3460.

* cited by examiner ated to be increasing by some 10% per annum, and a staggering 25% of which are revisions of failed implants [Graves, S. E., et al., The Australian Orthopaedic Association National Joint Replacement Registry. *Med. J. Aust.*, 2004; 180 (5 Suppl.): p. S31-4]. Further complications arise in situations where bone stock is compromised, or where initial implant stability is questionable (e.g. elderly patients, post-traumatic injuries or in revision operations), in which cases short- and long-term clinical results are typically inferior. The increases in life expectancy, and in the number of younger patients requiring implants, highlights the need for greater implant longevity and has driven biomedical research to develop novel micro-engineered surfaces to anchor the cementless prosthesis directly to the living bone through osseo-integration, thereby attempting to provide a stable interface strong enough to support life-long functional loading. It is clear that there is a serious problem with the longevity of current orthopaedic devices; a problem that is anticipated to only increase with the increasing demand from the ageing population requiring such treatments. It is clear that any improvement that could be made to increase the performance of these orthopaedics devices would be welcomed, not only by the orthopaedic community but also by the patients themselves.

BIOCOMPATIBLE MATERIAL AND USES THEREOF

FIELD OF THE INVENTION

The present invention relates to a biocompatible material and in particular to a biocompatible calcium silicate based material. In one embodiment the invention has been developed for use in tissue regeneration, including bone tissue. In other embodiments the invention has been developed as a suitable coating to improve the long-term stability of prior art implantable medical devices. In another embodiment the invention is suitable for use in drug delivery. However, it will be appreciated that the invention is not limited to these particular fields of use.

BACKGROUND OF THE INVENTION

The following discussion of the prior art is provided to place the invention in an appropriate technical context and enable the advantages of it to be more fully understood. It should be appreciated, however, that any discussion of the prior art throughout the specification should not be considered as an express or implied admission that such prior art is widely known or forms part of common general knowledge in the field.

Joint replacement therapy remains the only treatment available for relieving the pain and suffering in advanced degenerative bone disease. However, the technologies available in this area of orthopaedics are far from satisfactory. For example, Australians require more than 60,000 hip and knee replacement operations annually, a rate that has been estimated to be increasing by some 10% per annum, and a staggering 25% of which are revisions of failed implants [Graves, S. E., et al., The Australian Orthopaedic Association National Joint Replacement Registry. *Med. J. Aust.*, 2004; 180 (5 Suppl.): p. S31-4]. Further complications arise in situations where bone stock is compromised, or where initial implant stability is questionable (e.g. elderly patients, post-traumatic injuries or in revision operations), in which cases short- and long-term clinical results are typically inferior. The increases in life expectancy, and in the number of younger patients requiring implants, highlights the need for greater implant longevity and has driven biomedical research to develop novel micro-engineered surfaces to anchor the cementless prosthesis directly to the living bone through osseo-integration, thereby attempting to provide a stable interface strong enough to support life-long functional loading. It is clear that there is a serious problem with the longevity of current orthopaedic devices; a problem that is anticipated to only increase with the increasing demand from the ageing population requiring such treatments. It is clear that any improvement that could be made to increase the performance of these orthopaedics devices would be welcomed, not only by the orthopaedic community but also by the patients themselves.

Over the last century, various ceramics have been investigated for the purpose of encouraging or stimulating bone growth. For example, in the 1880's calcium sulphate (plaster of Paris) was utilised, however calcium sulphate displays a relatively low bioactivity and a relatively high rate of degradation (Tay et al., *Orthop. Clin. North Am.*, 1999, 30:615-23). In the 1950's hydroxyapatite was utilised, however hydroxyapatite suffers from a relatively low degradation rate and poor mechanical properties (Wiltfang J., et al *J. Biomed. Mater. Res.* 2002; 63:115-21). In the 1970's Bioglass® was developed, however, this material is relatively hard to handle due to its inherent brittleness and has a relatively low bending strength (Cordioli G., *Clin. Oral Implants Res.* 2001, 13:655-65). In the 1990's calcium silicate ceramics began to be used for stimulating bone growth. However these materials display relatively high degradation rates and high pH's in vivo, which tends to retard cell growth and affects osseointegration ability. Whilst other more recent ceramics such as HAp, Bioverit®, Ceraverit® and other calcium silicates have been found to bond to living bone and meet wide clinical applications, i.e. good bioactivity, they cannot be used in highly loaded areas, such as the cortical bone found in, for example, legs, due to the relative brittleness of these materials. For at least this reason such materials typically find their use as coatings on metallic implants.

Bone, as a living tissue, has the ability to heal itself, however in some cases damage to the bone from whatever cause is too severe to allow natural healing to take place, and so a bone graft is required to stimulate regeneration. There are three main types of bone grafts: autografts, allografts and synthetic grafts. Significant research is being conducted in the field of synthetic grafts as bone substitutes since synthetic grafts can ameliorate many of the problems associated with autografts and allografts, such as limited supply, donor site pain, and immunogenicity issues.

It is an object of the present invention to overcome or ameliorate at least one of the disadvantages of the above mentioned prior art, or to provide a useful alternative.

SUMMARY OF THE INVENTION

According to a first aspect, the present invention provides a biocompatible ceramic material comprising Baghdadite. Preferably the Baghdadite is synthetic Baghdadite or synthetically prepared Baghdadite.

According to a second aspect, the present invention provides use of Baghdadite as a biocompatible ceramic material.

As the skilled person will be aware, Baghdadite is a calcium zirconium silicate ceramic mineral having molecular formula $Ca_3ZrSi_2O_9$. For the purposes herein the terms Baghdadite, calcium zirconium silicate, bioceramic of the invention, and the molecular formula $Ca_3ZrSi_2O_9$ are considered to be synonymous. It will be appreciated that some substitution of the zirconium is possible with, say, titanium. For example the molecular formulae of Baghdadite could be represented as $Ca_3Zr_{0.75}Ti_{0.25}Si_2O_9$. Baghdadite could also be represented as $Ca_3(Zr_{0.89}Ti_{0.11})(Si_{1.98}Fe_{0.01})O_9$, as discussed in Al-Hermezi et al (Al-Hermezi, H. M., McKie, and D., Hall, A. J., *Mineralogical Mag., Baghdadite, a new Calcium Zirconium Silicate Mineral from Iraq*, March (1986), vol. 50, pp 119-23) which is incorporated herein by reference. However, it will be appreciated that the present invention relates to the ceramic mineral Baghdadite in all its forms and/or substitutions. For example, as shown above titanium or hafnium could be incorporated into the mineral as a partial replacement for the zirconium. Magnesium, strontium and possibly sodium could partially replace the calcium. A generalised formula for Baghdadite could be represented as per the following:

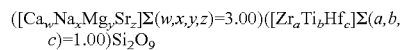

$$([Ca_wNa_xMg_ySr_z]\Sigma(w,x,y,z)=3.00)([Zr_aTi_bHf_c]\Sigma(a,b,c)=1.00)Si_2O_9$$

wherein:

w is in the range 2.00 to 3.00 and (x+y+z) making the balance; and a is in the range 0.50 to 1.00 and (b+c) making the balance.

The person skilled in the art would expect to be able to substitute elements as per the above generalised Baghdadite formula and still expect to maintain the structure and bioactivity. The skilled person will also appreciate that small amounts of impurities of other transition metals may be present in the ceramic material.

Preferably the biocompatible $Ca_3ZrSi_2O_9$ ceramic material of the invention comprises a transmission X-ray diffraction pattern having the following diffraction angles 2θ:
lines of strong intensity: 31.385; 31.075 and 29.940 degrees, and
lines of medium intensity: 27.662; 36.045 and 36.997 degrees.

Preferably the biocompatible calcium zirconium silicate ceramic material of the invention comprises a transmission X-ray diffraction pattern as per FIG. 1 or 2.

The skilled person will appreciate the term "biocompatible" defining a two-way response, i.e. the body's response to the ceramic material and the material's response to the body's environment. The biocompatibility of a medical device refers to the ability of the device to perform its intended function, with the desired degree of incorporation in the host, without eliciting any undesirable local or systemic effects in that host.

In preferred embodiments the biocompatible material of the invention is a medical grade or an implant grade material. In one embodiment, the biocompatible material is essentially "pure", comprising a purity of greater than about 95%, and more preferably greater than about 99%. Preferably the purity is greater than about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99%. It will be appreciated that preferably the calcium zirconium silicate of the invention is synthetically prepared.

Preferably the calcium zirconium silicate has a biocompatibility when placed in physiological fluid. Preferably the biocompatible material of the invention forms a hydroxyapatite layer upon exposure to bodily fluids. As the skilled person will appreciate, the formation of hydroxyapatite is widely recognised as strong evidence that the body accepts the material as sui generis and is a requirement for the implant to chemically bond with living bone and tissue.

Whilst in preferred embodiments the biocompatible calcium zirconium silicate material of the invention is pure, in other embodiments the material includes impurities, which may be in significant quantities. However, if impurities are present the impurities themselves are preferably biocompatible and/or do not result in a substantial overall reduction in biocompatibility. In other words, as the skilled person will appreciate, some tolerance to impurities may be acceptable. In one aspect, the biocompatible material of the invention is a combination of calcium zirconium silicate crystals intermixed with apatite or tricalcium phosphate crystals.

The first publication of the identification and analysis of the calcium zirconium silicate mineral described in the present invention was by Al-Hermezi et al. The mineral was named Baghdadite in recognition of its place of discovery (after Baghdad, the capital of Iraq). Naturally occurring Baghdadite is extremely rare, and was discovered in melilite skarn in contact with banded diorite, in roof pendant xenoliths of calc-silicate marbles and hornfels. Baghdadite is related crystallographically and chemically to the wöhlerite group of minerals, comprising cuspidinem lÅvenite, rosenbuschite, hiortdahlite, wöhlerite and niocalite. The ideal composition of Baghdadite is $Ca_3Zr[O_2]Si_2O_7$, however is typically expressed as $Ca_3ZrSi_2O_9$, and is distinguished from the rest of the wöhlerite group by the absence of significant $F^-$ and $OH^-$ ions. For the purposes of the present invention, the terms Baghdadite and calcium zirconium silicate, and the molecular formula $Ca_3ZrSi_2O_9$, are considered to be synonymous.

Whilst calcium zirconium silicate is an extremely rare naturally occurring substance, the present disclosure is the first time that the calcium zirconium silicate material of the invention has been synthetically prepared and its potential use as a biocompatible material explored. It has been found that, surprisingly, calcium zirconium silicate displays exceptional biocompatibility, and more particularly, is particularly suited for the regeneration of bone and other tissue. In one embodiment, the inventors contemplate that the biocompatible calcium zirconium silicate of the invention finds particular utility in resurfacing arthritic joints to promote the growth of articular cartilage. In other embodiments, the biocompatible material of the invention is useful in the development of 3D scaffolds which promote migration, proliferation and differentiation of bone and endothelial cells, for example in orthopaedic and maxillofacial surgeries, and yet provides sufficient mechanical properties for load-bearing parts. The calcium zirconium silicate material of the invention also supports bone tissue regeneration/formation and vascularization, and yet also provides minimal fibrotic reactions. In one aspect, the present invention provides biphasic scaffolds for osteochondral defects. In yet other embodiments, the present invention provides a calcium zirconium silicate which is coatable on currently used orthopaedic and dental implants to provide enhance long-term implant stability. In further embodiments the calcium zirconium silicate mineral of the invention is selectively coatable on currently used orthopaedic implants, for example on areas where wear is an issue.

As discussed previously, the development of bioglass, glass-ceramics, and bioceramics containing CaO and $SiO_2$ for bone tissue regeneration has received great attention in the past 3 decades. The stimulatory effect of the Ca and Si containing ionic products released from materials on osteoblast proliferation, differentiation, and related gene expression, and mineralization have also been well documented (see for example Xynos I. D., et al in *Ionic products of bioactive glass dissolution increase proliferation of human osteoblasts and induce insulin-like growth factor II mRNA expression and protein synthesis*, Biochem. Biophy. Res. Commun. 2000; 276:461-465). $CaSiO_3$ based materials are considered as potential bioactive materials for bone tissue regeneration and implant coatings due to their bioactivity. However, a major drawback of the $CaSiO_3$ ceramics is their relatively high dissolution rate leading to a high pH value in the surrounding environment, (see for example Siriphannon P, et al in *Formation of hydroxyapatite on $CaSiO_3$ powders in simulated body fluid*, J Eur. Ceram. Soc. 2002; 22:511-520). Indeed, the bonding of $CaSiO_3$ coatings to titanium substrate degrades with the increasing immersion time in simulated body fluid (SBF) due to the relatively fast dissolution rate of the coating, which limits further biological applications. It has been unexpectedly found that the chemical modification of calcium silicate with the element zirconium to produce a calcium zirconium silicate, and in particular Baghdadite, provides a bioceramic with significantly improved properties compared to previously known calcium silicates and previously known bioceramic materials.

In particular, the biocompatible calcium zirconium silicate of the invention provides many of the advantages of the $CaSiO_3$ materials but ameliorates many of its disadvantages. The calcium zirconium silicate displays a relatively reduced dissolution profile, which is associated with a relatively reduced pH compared to $CaSiO_3$ materials. Further, calcium zirconium silicate exhibits excellent mechanical properties and allows attachment and proliferation of bone cells. In particular, the calcium zirconium silicate of the invention has been found to form a chemical bond with bone, and the ability to form an apatite layer. Furthermore it is believed that the calcium zirconium silicate of the invention displays relatively reduced corrosion in biological environments.

According to a third aspect the present invention provides a method for the preparation of a biocompatible ceramic material, comprising the steps of: providing a sol of precursor materials for producing calcium zirconium silicate, at least partially gelling the sol, and drying and sintering said at least partially gelled sol to thereby form Baghdadite.

Preferably the purity of the calcium zirconium silicate produced by the method according to the second aspect is at least 95%, and more preferably at least 99%. Preferably the purity is greater than about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99%.

Preferably the biocompatible calcium zirconium silicate ceramic material when produced by the method according to the second aspect comprises a transmission X-ray diffraction pattern having the following diffraction angles 2θ:
  lines of strong intensity: 31.385; 31.075 and 29.940 degrees, and
  lines of medium intensity: 27.662; 36.045 and 36.997 degrees.

The calcium zirconium silicate ceramic of the invention comprises the molecular formula $Ca_3ZrSi_2O_9$, and according to the second aspect is sol-gel derived. However, it will be appreciated that in other embodiments any method of synthetic production of the calcium zirconium silicate would fall within the purview of the present invention. For example, in another embodiment, $SiO_2$, $CaO$ and $ZrO_2$ may be melted at relatively high temperatures (for example see the methodology outlined in Mazerolles, L. et al. *Aerospace Science and Technology*, 2008; 12(7):499-505) and then cooled, and the resulting material pulverized. The resulting powder can then be formed and hot-pressed, as is well known in the art, for example (see Russias J et al. *Journal of the European Ceramic Society*, 2007; 27(0:327-335).

According to a fourth aspect the present invention provides a biocompatible calcium zirconium silicate ceramic when produced by the method according to the third aspect.

According to a fifth aspect the present invention provides an implantable medical device comprising biocompatible Baghdadite. Preferably the Baghdadite is synthetic.

The medical device is preferably chosen from the group consisting of: a 3D implantable scaffold, an orthopaedic implant for reconstructive surgery, a dental implant/prostheses, a spine implant, implants for craniofacial reconstruction and alveolar ridge augmentation, for cartilage regeneration, an osteochondral defect implant, a strut, a stent or a stent-graft. However, it will be appreciated that there are many other devices which would be within the purview of the present invention. The skilled person will readily appreciate how to manufacture a medical device from the biocompatible material of the invention. For example the inventors contemplate that the biocompatible material of the invention can be formed into a medical device in a similar methodology as outlined in the prior art, for example see Hench L. L. *J. Am. Ceram. Soc.* 1991; 74: 1487-1510; and Zhao J. et al. *Biomed. Mater.* 2006; 1 (4): 188-92.

Bone implant comprising the bioceramic material of the invention.

Tooth filling implant comprising the bioceramic material of the invention.

Biocement comprising the bioceramic material of the invention.

A composite biocompatible material comprising Baghdadite.

In other embodiments, the bioactive calcium zirconium silicate ceramic of the invention may be formed into a surgical device or as a coating on a surgical device. For example, Ti-6A1-4V, a titanium alloy, is well established as one of the primary biomaterials for orthopaedic implants because of its excellent biocompatibility, low toxicity, high chemical stability, low rate of corrosion and favourable mechanical properties. However, Ti-6A1-4V has a crucial drawback: poor wear resistance. Adhesive and abrasive wear at the bone—implant interface and articulating surfaces generates debris. This debris—small particles and shards of metal that detach from the implant surface—enter the surrounding tissue and migrate into spaces between the bone and implant where they induce inflammation and associated bone destruction, leading to aseptic loosening. This jeopardises the stability of the prosthesis, leading to the premature failure of the device, as well as pain and disability in patients [Haynes, D. R., T. N. Crotti, and H. Zreiqat, *Regulation of osteoclast activity in peri-implant tissues*. Biomaterials, 2004. 25(20): p. 4877-85]. As a result, global failure rates of orthopaedic implants, mainly hip and knee replacements, are unacceptably high. The success of orthopaedic implants depends on strong anchorage of the device material in bone tissue. Various biomaterials modifications have been applied in an attempt to enhance bone formation, but to date none forms a stable interface with the strength required to support functional loading for the lifetime of the patient. Ideally, the implant should also interact with the host tissue, recruiting and even promoting differentiation of osteogenic cells, rather than acting as a passive stage for the performance of any itinerant cells. An important factor in selecting orthopaedic implant material, therefore, is identifying the correct chemistry to support or stimulate an appropriate host response. Frequently implant materials are not preferentially compatible with bone cells responsible for bone formation; rather, they promote the formation of undesirable soft connective tissue by other cells such as fibroblasts. Considerable effort has gone into developing surface treatments and coatings to improve host tissue-implant integration. Although these approaches have had some success, they have been shown to have slow rates of osseointegration and poor mechanical anchorage in challenging clinical cases, such as those associated with large bone loss and poor bone quality [see for example Sporer, S. M. and W. G. Paprosky, *Biologic fixation and bone ingrowth. Orthop Clin North Am*, 2005. 36(1): p. 105-11, vii]. During the last two decades, various surface modification methods have been proposed to improve bone conductivity or bioactivity of Ti-6A1-4V by coating it with ceramic. The aim has been to enhance osseo-integration and thereby interlock the implant with the surrounding skeletal tissue, providing a stable interface strong enough to support life-long functional loading. The coating should prevent corrosion of the underlying substrate in a biological environment; create a barrier against the release of the toxic metal debris into the body [Sun, L., et al., *Material fundamentals and clinical performance of plasma-sprayed hydroxyapatite coatings: a review*. J Biomed Mater Res, 2001. 58(5): p. 570-92]; and combine the mechanical properties of the metal with the bioactivity of the ceramic. One such approach is to coat Ti-6A1-4V with bioactive ceramics such as hydroxyapatite (HAp) and calcium silicate ceramics ($CaSiO_3$) [Harle, J., et al., *Initial responses of human osteoblasts to sol-gel modified titanium with hydroxyapatite and titania composition*. Acta Biomater, 2006. 2(5): p. 547-56]; [Balani, K., et al., *Tribological behavior of plasma-sprayed carbon nanotube-reinforced*

*hydroxyapatite coating in physiological solution.* Acta Biomater, 2007. 3(6): p. 944-51]; [Xue, W., et al., *In vivo evaluation of plasma-sprayed wollastonite coating.* Biomaterials, 2005. 26(17): p. 3455-600]; [Liu, X., C. Ding, and Z. Wang, *Apatite formed on the surface of plasma-sprayed wollastonite coating immersed in simulated body fluid.* Biomaterials, 2001. 22(14): p. 2007-12]. HAp has been used to coat hip-joint endoprostheses for the enhancement of long-term fixation in femoral bone [Ha, S. W., et al., *Chemical and morphological changes of vacuum-plasma-sprayed hydroxyapatite coatings during immersion in simulated physiological solutions.* J Am Ceram Soc 1998. 81 p. 81-8]. These have been shown to improve the stability of the Ti-6A1-4V implant, the interface strength, the bone mineralization, and the bone ingrowth rate [Soballe, K., et al., *Gap healing enhanced by hydroxyapatite coating in dogs.* Clin Orthop Relat Res, 1991 (272): p. 300-7]. It is contemplated that the biomaterial/bioceramic of the present invention, which has improved properties compared to these prior art coatings, will provide a coated implant having improved service life and excellent osseointegration.

In one embodiment, the medical device is permanently implanted.

In one embodiment, the medical device is substantially biodegradable.

In one embodiment the porosity of the medical device comprising a biocompatible material of the invention is between about 20 to about 30%. However, it will be appreciated that the device could be configured to have lower or greater porosity according to the intended or desired use, and any porosity range would be within the purview of the present invention. For example porosities of 10, 15, 20, 25, 30, 35, 40, 45, 50, 55, 60, 65, 70, 75 or 80% are possible.

In one embodiment, the pore size of the device is between about 75 to about 200 µm. However, it will be appreciated that the device could be configured to have lower or greater pore size according to the intended or desired use, and any pore size would be within the purview of the present invention. For example, pore sizes of 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or 500 micron are possible. As the skilled person will appreciate, the porosity of ceramics can be adjusted by controlling the content and size of porogens. The compressive strength of the porous ceramics of the invention are between 1.8 to 5.1 MPa with porosities between 65 to 78%. This is ideal for scaffolds to be placed in load-bearing applications as the strength of the natural bone is within this range.

Implantable devices according to the present invention have many properties that make them suitable for use as implants, including high mechanical strength, resistance to fatigue, corrosion resistance, and biocompatibility. The implants may be implanted in animals, non-limiting examples of which include reptiles, birds, and mammals, with humans being particularly preferred.

The devices of this invention may be implanted into a body in different ways, including, but not limited to subcutaneous implantation, implantation at the surface of the skin, implantation in the oral cavity, use as sutures and other surgical implantation methods.

In one embodiment, the calcium zirconium silicate device of the present invention may be coated with at least one resorbable polymer material, non-limiting examples of which include polyglycolides, polydioxanones, polyhydroxyalkanoates, polylactides, alginates, collagens, chitosans, poly-alkylene oxalate, polyanhydrides, poly(glycolide-co-trimethylene carbonate), polyesteramides, or polydepsipeptides etc.

Alternatively, the coating material may comprise healing promoters such as thrombosis inhibitors, fibrinolytic agents, vasodilator substances, anti-inflammatory agents, cell proliferation inhibitors, and inhibitors of matrix elaboration or expression. Examples of such substances are discussed in U.S. Pat. No. 6,162,537. The present invention also contemplates using a polymer coating, (e.g. a resorbable polymer) in conjunction with a healing promoter to coat the implantable medical device, for example according to the reference [Wu C. *Acta Biomateilia,* 2008; 4:343-353].

According to a sixth aspect the present invention provides a method for producing an implantable medical device comprising: transferring Baghdadite onto a substrate thereby forming said implantable medical device.

It will be appreciated that there are a number of methods of transferring a biocompatible calcium zirconium silicate onto a supporting surface or substrate, and any of these methods fall within the purview of the present invention. For example, in one embodiment, the calcium zirconium silicate is plasma spray coated. As is well known in the art, this method essentially comprises the steps of spraying molten or heat softened material onto a surface to provide the coating. The material, in the form of powder, is injected into a high temperature plasma flame, where it is rapidly heated and accelerated to a high velocity. The hot material impacts on the substrate surface and rapidly cools thereby forming a coating (see for example Wu C. et al. J R Interface Soc. 2008; in Press; and Liu X. *Biomedicine &Pharmacotherapy* 2008; 62(8):526-529). The coatings have a dense structure with a thickness of about 50 µm.

According to a seventh aspect the present invention provides an implantable drug delivery device comprising calcium zirconium silicate. It will be appreciated that the drug delivery device can deliver any drug and the can be shaped to suit the particular application. For example see Krajewski et al in *J. Mater. Sci.: Mater. In Med.* 12 (2006) 763-771.

According to an eighth aspect the present invention provides an implantable medical device having a predetermined dissolution profile comprising a predetermined quantity of Baghdadite. For example, in one embodiment it is envisaged that the implantable drug delivery device could have a dissolution profile of Si ions as follows:

| Time (h) | released (%) |
| --- | --- |
| 2 | 0.02 |
| 12 | 0.96 |
| 24 | 0.19 |
| 48 | 0.28 |
| 72 | 0.55 |
| 168 | 1.18 |

Whilst the above dissolution profile is a single example, it will be appreciated by the skilled person that other dissolution profiles will fall within the purview of the present invention.

According to a ninth aspect the present invention provides a method for modifying the dissolution profile of a calcium silicate based medical device comprising: at least partially producing the device from a biocompatible Baghdadite.

According to a tenth aspect the present invention provides a method for improving the long term stability of an implantable medical device comprising the step of: coating the device with Baghdadite.

Preferably the coating includes a biocompatible polymer, which in one embodiment is PLGA. In one aspect the implantable medical device is a biphasic scaffold for an osteochondral defect.

According to an eleventh aspect the present invention provides use of calcium zirconium silicate in the regeneration or resurfacing of tissue, comprising contacting the tissue with a quantity of Baghdadite for a sufficient period to at least partially effect said regeneration or resurfacing.

According to a twelfth aspect the present invention provides a method for regenerating or resurfacing tissue, comprising the step of: contacting said tissue with Baghdadite.

According to a thirteenth aspect the present invention provides a method for forming osseous tissue on an orthopaedic defect, comprising the step of: contacting said defect with Baghdadite. The present inventors contemplate that the defect could be contacted with, for example, a cementing paste comprising Baghdadite and cured or allowed to set. The presence of the biocompatible Baghdadite would act to stimulate the formation of the osseous tissue on the orthopaedic defect.

According to a fourteenth aspect the present invention provides a method for treating orthopaedic conditions comprising, contacting a patient in need of such treatment with an effective regenerating amount of biocompatible composition comprising Baghdadite.

According to a fifteenth aspect the present invention provides a kit for regenerating or resurfacing tissue, comprising Baghdadite and a therapeutic agent which stimulates and accelerates tissue regeneration. Such therapeutic agents are well known the art.

According to a sixteenth aspect the present invention provides a method for the preparation of a calcium silicate based biocompatible material, comprising the steps of: chemically modifying said calcium silicate based biocompatible material with zirconium.

In one embodiment, preferably the biocompatible calcium zirconium silicate material of the invention is a fully synthetic bone graft substitute. Due to its interconnected pores, the material serves as an ideal osteoconductive scaffold and supports the formation of new host bone. As highlighted above, many of the advantages of the new material can be summarised as follows:

Optimized porosity
Enhanced bone ingrowth and vascularization
Avoids potential problems common for grafting methods
Is formable to almost any shape to suit the application
Easy to use
Combines with autologous bone marrow or blood
Displays accelerated and enhanced osteointegration The uses of the present invention are manyfold, including:
For bone void fillings or augmentation in zones requiring cancellous rather than cortical bone
For the filling of bone defects after trauma, reconstruction, or correction in non-load or load-bearing indications
For trauma and orthopaedics: Filling of voids caused by cysts or osteotomies, filling of defects arising from impacted fractures, refilling of cancellous bone-harvesting sites, arthrodesis and non-unions
For spine surgery: Postero-lateral fusion, interbody fusion (as cage-filling material), vertebrectomies (as filling material of the vertebral implants), refilling of bone graft-harvesting sites
For cranio-maxillofacial surgery: Reconstruction of mandibular defects and sinus lifts

BRIEF DESCRIPTION OF THE DRAWINGS

This patent or application file contains at least one drawing executed in color. Copies of this patent or patent application publication with color drawing(s) will be provided by the Office upon request and payment of the necessary fee.

Preferred embodiments of the invention will now be described, by way of example only, with reference to the accompanying drawings in which.

DEFINITIONS

Figure 1:
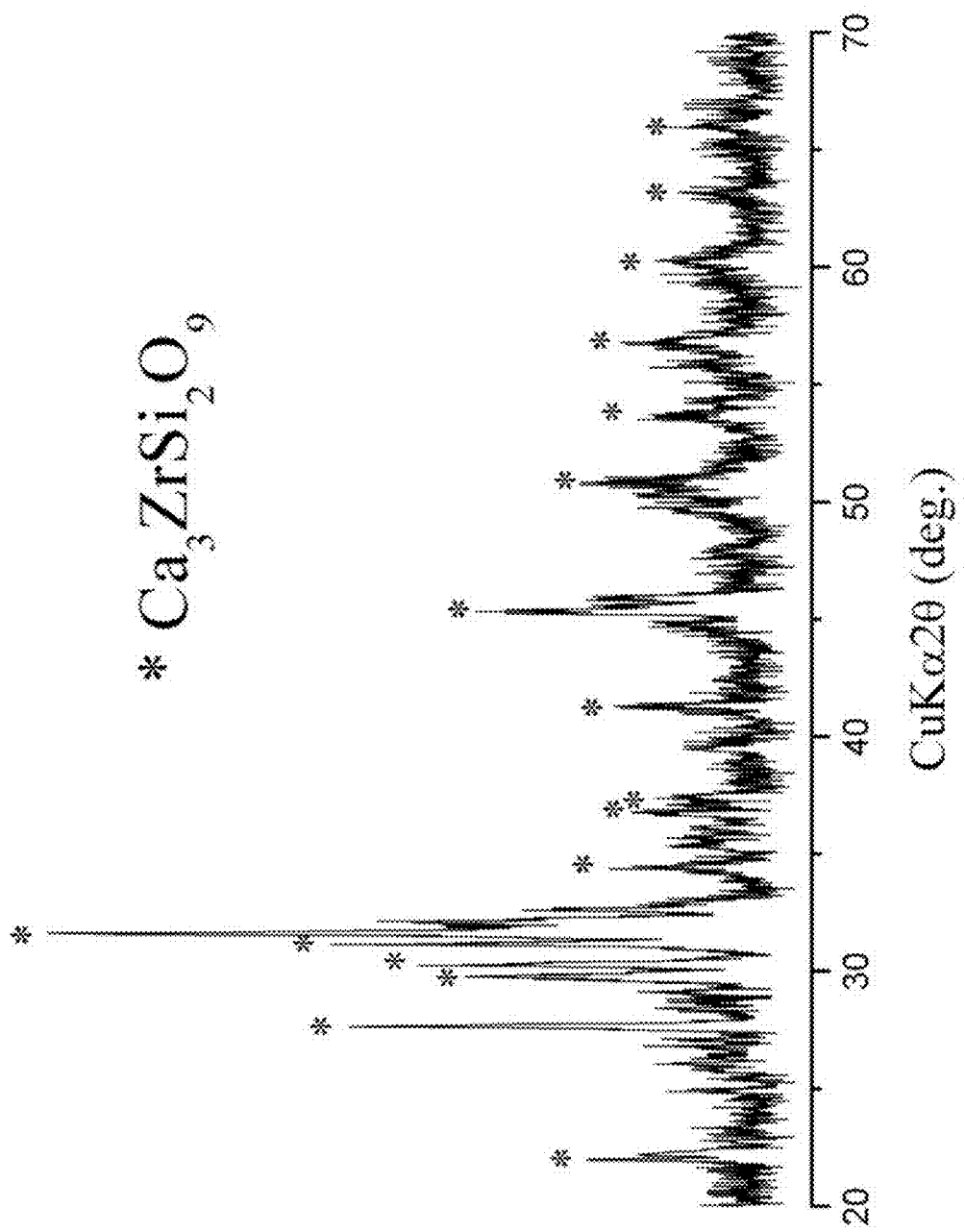
FIG. 1 is an XRD analysis pattern of calcium zirconium silicate material in powder form, highlighting the peaks characteristic of the material.

In describing and claiming the present invention, the following terminology will be used in accordance with the definitions set out below. It is also to be understood that the terminology used herein is for the purpose of describing particular embodiments of the invention only and is not intended to be limiting. Unless defined otherwise, all technical and scientific terms used herein have the same meaning as commonly understood by one having ordinary skill in the art to which the invention pertains.

The recitation of a numerical range using endpoints includes all numbers subsumed within that range (e.g., 1 to 5 includes 1, 1.5, 2, 2.75, 3, 3.80, 4, 5, etc.).

The terms "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, an "implant" refers to an article or device that is placed entirely or partially into an animal, for example by a surgical procedure.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to".

Other than in the operating examples, or where otherwise indicated, all numbers expressing quantities of ingredients or reaction conditions used herein are to be understood as modified in all instances by the term "about". The examples are not intended to limit the scope of the invention. In what follows, or where otherwise indicated, "%" will mean "weight %", "ratio" will mean "weight ratio" and "parts" will mean "weight parts".

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviations found in their respective testing measurements.

PREFERRED EMBODIMENT OF THE INVENTION

Preferred embodiments of the present invention will be described in the following.

Material Preparation $Ca_3ZrSi_2O_9$ powders were synthesized by sol-gel method using zirconia oxide nitrate [$ZrO(NO_3)_2$, Sigma-Aldrich, USA], calcium nitrate tetrahydrate [$Ca-(NO_3)_2.4H_2O$, Sigma-Aldrich, USA] and tetraethyl orthosilicate (TEOS) [$(C_2H_5O)_4Si$, Sigma-Aldrich, USA] as raw materials. Briefly, TEOS was mixed with ethanol and 2 M $HNO_3$ (mol ratio: $TEOS/ethanol/HNO_3$=1:8:0.16) and hydrolyzed for 30 min under stirring. Then, the $ZrO(NO_3)_2$ and $Ca(NO_3)_2.4H_2O$ were added into the mixture (mol ratio: $ZrO(NO_3)_2/Ca(NO_3)_2.4H_2O/TEOS$=1:3:2) respectively, and reactants were stirred for 5 h at room temperature (RT). After the reaction, the clear solution was maintained at 60° C. for 1 day and dried at 100° C. for 2 days to obtain the dry gel. The dry gel was calcined at 1150° C. for 3 h.

For the preparation of ceramic disks, the calcined $Ca_3ZrSi_2O_9$ powders were sieved to 230 meshes and then were mixed with 6% (w/v) polyvinyl alcohol (PVA, Sigma-Aldrich, USA) water solution binders (weight ratio: PVA solution/powders=1:9). The mixture was uniaxially pressed at 200 MPa to produce $Ca_3ZrSi_2O_9$ green disks with a dimension of Ø15×2 mm. Subsequently, the green disks were sintered at 1400° C. for 3 h with a heating rate of 2° C./min to obtain the ceramic disks. The sintered $Ca_3ZrSi_2O_9$ ceramic disks were analysed using X-ray diffraction (XRD, Siemens D5000, Germany). $CaSiO_3$ disks were prepared using the same method to provide the control material, as originally described in Wu C, Ramaswamy Y, Chang J, Woods J, Chen Y, Zreiqat H. *The effect of Zn contents on phase composition, chemical stability and cellular bioactivity in Zn—Ca—Si system ceramics. J Biomed. Mater. Res. B. Appl. Biomater.* 2008.)

Surface roughness of $Ca_3ZrSi_2O_9$ and $CaSiO_3$ ceramics was determined using a surface test apparatus (Surftest 402, Mitutoyo Japan). Five different tracks on each disk and three disks of each material were measured and used to calculate an average roughness value (Ra, m).

Apatite-Formation Ability of $Ca_3ZrSi_2O_9$ Ceramics in Simulated Body Fluid (SBF)

SBF containing ion concentrations similar to those found in human blood plasma was prepared as previously described (Wu C, Ramaswamy Y, Kwik D, Zreiqat H. *The effect of strontium incorporation into $CaSiO_3$ ceramics on their physical and biological properties. Biomaterials* 2007; 28(21): 3171-81). Briefly, reagent-grade $CaCl_2$, $K_2HPO_4.3H_2O$, NaCl, KCl, $MgCl_2.6H_2O$, $NaHCO_3$, and $Na_2SO_4$ in appropriate amounts were dissolved in distilled water and pH adjusted to 7.4. $Ca_3ZrSi_2O_9$ ceramic disks were soaked in SBF at 37 for 14 days, and the ratio of disc surface area to solution volume of SBF was 0.1 $cm^2$/ml. The soaked disks were dried at 100° C. for 1 day and characterized using scanning electron microscopy (SEM) coupled with energy dispersive spectrometer (EDS, Philips XL 30 CP, Netherlands).

Isolation and Culture of Primary Hob

HOB were isolated from normal human trabecular bone as previously described (Zreiqat H, Valenzuela S M, Nissan B B, Roest R, Knabe C, Radlanski R J, et al. *The effect of surface chemistry modification of titanium alloy on signalling pathways in human osteoblasts. Biomaterials* 2005; 26(36):7579-86). Briefly, bone was divided into 1 $mm^3$ pieces, washed several times in phosphate buffered saline (PBS), and digested for 90 min at 37° C. with 0.02% (w/v) trypsin (Sigma-Aldrich, USA) in PBS. Digested cells were cultured in complete media containing a-Minimal Essential Medium (α-MEM, Gibco Laboratories, USA), supplemented with 10% (v/v) heat-inactivated fetal calf serum (FCS, Gibco Laboratories, USA), 2 mM L-glutamine (Gibco Laboratories, USA), 25 mM Hepes Buffer (Gibco Laboratories, USA), 2 mM sodium pyruvate, 30 mg/ml penicillin, 100 mg/ml streptomycin (Gibco Laboratories, USA) and 0.1 M L-ascorbic acid phosphate magnesium salt (Wako Pure Chemicals, Osaka, Japan). The confluent cells were used to determine HOB attachment, proliferation, differentiation and their gene regulation. Permission to use discarded human tissue was granted by the Human Ethics Committee of the University of Sydney and obtained with appropriate informed consent.

Attachment of HOB

HOB seeded at cell density of $1.5\times10^4$ cells/$cm^2$ on $Ca_3ZrSi_2O_9$ and $CaSiO_3$ disks were allowed to attach for 1, 3 and 7 days. At the end of each time point cells were fixed with 1.25% glutaraldehyde, 4% paraformaldehyde and 4% sucrose and post fixed in 1% osmium tetroxide followed by sequential dehydration in graded ethanol (70%, 90%, 95% and 100%), before drying in hexamethyldisilizane and coating with gold for SEM analysis.

Cytoskeletal Organization

HOB seeded at cell density of $1.5\times10^4$ cells/$cm^2$ were grown on the ceramic disks for 24 h, before fixing in 3.7% paraformaldehyde. Rhodamine—conjugated phalloidin (Molecular Probes, USA) was added to the cells and incubated for 1 h in the dark followed by counter staining with DAPI to visualize the nucleus. Imageswere taken at 60× magnification with an inverted fluorescence microscope (Nikon Eclipse E800 fluorescence microscope).

Cytotoxicity Test

The $Ca_3ZrSi_2O_9$ and $CaSiO_3$ powder extracts were mixed in culture medium following the International Standard Organization (ISO/EN 10993-5) protocol. The dissolution extracts of ceramics were prepared by adding $Ca_3ZrSi_2O_9$ powders to serum-free a-MEM culture medium at a ratio of 200 mg/ml (powder to medium) and incubated at 37° C. for 24 h, then the mixture was centrifuged and the supernatant collected. Serial dilutions of extracts (100, 50, 25, 12.5 and 6.25 mg/ml) were prepared using serum-free a-MEM medium. HOB were seeded at cell density of $2.7 \times 10^4$ cells/cm$^2$ into 96-well plates and incubated for 24 h before culture medium was removed and replaced by 50 ml of a-MEM supplemented with 20% FCS and 50 ml of appropriate concentration of extracts. The culture medium supplemented with 10% FCS without the addition of diluted extracts was used as a blank control (Blank). Fifty microliter solution of 0.2% Triton X-100 and 50 mL a-MEM medium supplemented with 20% FCS was used as a negative control (Ctr−). Cells were then incubated for 1, 3 and 7 days and proliferation evaluated using MTS assay (Promega, Madison, Wis., USA) according to the manufacturer's instructions where 100 ml of 0.5 mg/ml MTS solution was added to each well and incubated for 4 h at 37° C. The absorbance was read at 490 nm using an ELISA plate reader and software Accent/MTS. The Si and Ca ions concentrations of the extracts were analysed using the Inductively Coupled Plasma Atomic Emission Spectroscopy (ICP-AES; Perkin-Elmer, Optima 300DV, USA) (Table 1).

TABLE 1

The Ca and Si ion concentrations of $Ca_3ZrSi_2O_9$ & $CaSiO_3$ extract (mM)

| Materials | Ions | Blank | 6.25 | 12.5 | 25 | 50 | 100 | 200 |
|---|---|---|---|---|---|---|---|---|
| $Ca_3ZrSi_2O_9$ | Ca | 0.18 | 0.46 | 0.75 | 1.33 | 2.48 | 4.78 | 9.34 |
| | Si | 0 | 0.002 | 0.006 | 0.011 | 0.022 | 0.041 | 0.091 |
| $CaSiO_3$ | Ca | 0.18 | 0.41 | 0.64 | 1.11 | 2.05 | 3.92 | 7.67 |
| | Si | 0 | 0.097 | 0.194 | 0.388 | 0.776 | 1.553 | 3.107 |

Proliferation of HOB

HOB cell proliferation was quantitatively assessed by MTS (3-(4,5-dimethylthiazol-2-yl)-2,5-diphenyltetrazoliumbromide) assay after 1, 3 and 7 days of culturing $2.7 \times 10^4$ cells/cm$^2$ on $Ca_3ZrSi_2O_9$ and $CaSiO_3$ substrates. Three disks of each type were tested for each culture time and proliferation was evaluated using MTS assay. Hundred microliter of the reacted reagent from each well was transferred to 96-well plate and the absorbance was recorded using a microplate reader (PathTech, Australia) at 490 nm using the software Accent.

Alkaline Phosphatase (ALP) Activity, Expression of HOB Related Genes

Alkaline phosphatase activity was evaluated for HOB seeded at cell density of $2.7 \times 10^4$ cells/cm$^2$ on $Ca_3ZrSi_2O_9$ and $CaSiO_3$ disks for 1, 3 and 7 days. For ALP activity, cell layer was washed gently, lysed in Tris buffer containing 0.2% NP-40 solution, sonicated, and centrifuged. Two microliter of the lysatewas added to 100 ml of 16.3 mM/L p-nitrophenol phosphate (ThermoFisher, USA) in 96-well plate and incubated for 30 min at 37° C. The reaction was stopped using 100 ml of 0.1 N NaOH and the absorbance read at 405 nm using a microplate reader (PathTech, Australia). ALP activity was calculated from a standard curve after normalizing to the total protein content, which was measured using Pierce BCA protein assay kit. Results were expressed in millimoles of p-nitrophenol produced per hour per milligram of protein.

HOB were seeded on $Ca_3ZrSi_2O_9$ and $CaSiO_3$ at a density of $1.0 \times 10^5$ cells/cm$^2$ and cultured for 1, 3 and 7 days to examine the expression of HOB related genes. Total RNA was isolated from HOB cultured in triplicates on each ceramic disk. The culture medium was collected from each well and the ions (Ca and Si) released from the materials and pH values of the culture medium were measured using ICP-AES and pH meter, respectively (Table 2A and 2B).

TABLE 2A

Comparative dissolution data for $Ca_3ZrSi_2O_9$ and $CaSiO_3$ over a 1 week period.

| Culture Time (days) | Ions | Ion Concentrations | | |
|---|---|---|---|---|
| | | $Ca_3ZrSi_2O_9$ (mM) | $CaSiO_3$ (mM) | TCP (mM) |
| 1 | Ca | 2.86 | 4.15 | 0.4 |
| | Si | 0.47 | 0.81 | 0 |
| | Zr | 0 | 0 | 0 |
| 3 | Ca | 5.25 | 6.14 | 0.9 |
| | Si | 0.88 | 1.13 | 0 |
| | Zr | 0 | 0 | 0 |
| 7 | Ca | 9.15 | 9.59 | 1.2 |
| | Si | 1.55 | 1.73 | 0 |
| | Zr | 0 | 0 | 0 |

TABLE 2B

Comparative pH data for $Ca_3ZrSi_2O_9$ and $CaSiO_3$ over a 1 week period.

| Culture Time | pH | | |
|---|---|---|---|
| (days) | $Ca_3ZrSi_2O_9$ | $CaSiO_3$ | TCP |
| 1 | 7.3 | 7.51 | 7.2 |
| 3 | 7.4 | 7.82 | 7.3 |
| 7 | 7.5 | 8.1 | 7.3 |

Human Osteoclast Culture (OC)

Human primary monocytes were isolated from buffy coats of healthy adult donors and differentiated into mature OC. Monocyte layer isolated from the buffy coat using the Ficoll-Paque gradient sedimentation was seeded on ceramic disks or dentine at a concentration of $5.3 \times 10^5$ cells/cm$^2$. Cells were left to adhere to the material for 24 h and non-adherent cells were removed and replaced with fresh complete medium consisting of α-MEM containing 10% FCS, 5 mg/ml penicillin and 50 U/ml of streptomycin and 1% L-glutamine, and supplemented with 25 ng/ml of macrophage colony stimulating factor (Chemicon, California) and 50 ng/ml recombinant human RANKL (Chemicon, California). Media was changed every 3 days and monocytes were allowed to differentiate into functional OC over a period of 21 days. OC differentiation was confirmed on glass cover slips by tartrate-resistant acid phosphatase (TRAP) staining and functional activity was confirmed by SEM analysis of dentine resorption pits.

Osteoclast Attachment, f-Actin and $a_v\beta_3$ Integrin Staining

Attachment of OC on $Ca_3ZrSi_2O_9$ and $CaSiO_3$ ceramics after 21 days was determined using SEM analysis as described previously. For $a_v\beta_3$ immunostaining, cells were fixed with 4% paraformaldehyde, permeabilised and the monoclonal antibody CD51 (Immunotech) (1:50 dilution in 0.2% BSA-PBS), was added and incubated for 1 h at RT. Rhodamine-phalloidin (Invitrogen), was then added to the cells and incubated in the dark for 1 h at RT to determine f-actin staining. The nucleus was stained with DAPI before confocal microscopy analysis (Nikon Eclipse E800 fluorescence microscope, Japan).

Endothelial Cell Culture, Attachment and ZO-1 Staining

Purified and immortalised human dermal microvascular endothelial cells (HMEC-1) were maintained in culture on 0.1%-gelatin-coated culture flasks and grown to confluence in DMEM/F12+L-glutamine+HEPES medium pH 7.4

(Gibco), supplemented with 10% heat-inactivated fetal calf serum (Gibco). For specific experiments, cells were detached by trypsin-EDTA treatment, and counted in trypan-blue before being seeded on 0.1% gelatin-coated $Ca_3ZrSi_2O_9$ and $CaSiO_3$ ceramic disks. The gelatin-coated step is necessary for these cells for even if they create their own matrix; they need a support to make confluent cobblestone monolayers as previously described. The HMEC-1 were seeded at a density of $2.4\times10^4$ cells/cm$^2$ and were allowed to attach onto the disks for 3 days (37° C., 5% $CO_2$) before SEM analysis. For characterization of the junctional proteins ZO-1, cells were left to grow on the disks for 7 days, the confluent cells were washed, fixed in 4% paraformaldehyde and permeabilized in 0.1% Triton X-100. The primary antibody (Mouse anti-ZO-1, Zymed Labs 1:50 in 0.2% BSA-PBS) was added to the cells and incubated for 1 h at RT followed by incubation for 45 min with the secondary antibody (Alex fluor 488 goat anti mouse 1:100). The nucleus was stained with DAPI and disks were analysed using confocal microscopy (Nikon Eclipse E800 fluorescence microscope, Japan).

Characterization of the Ceramics

Figure 2:
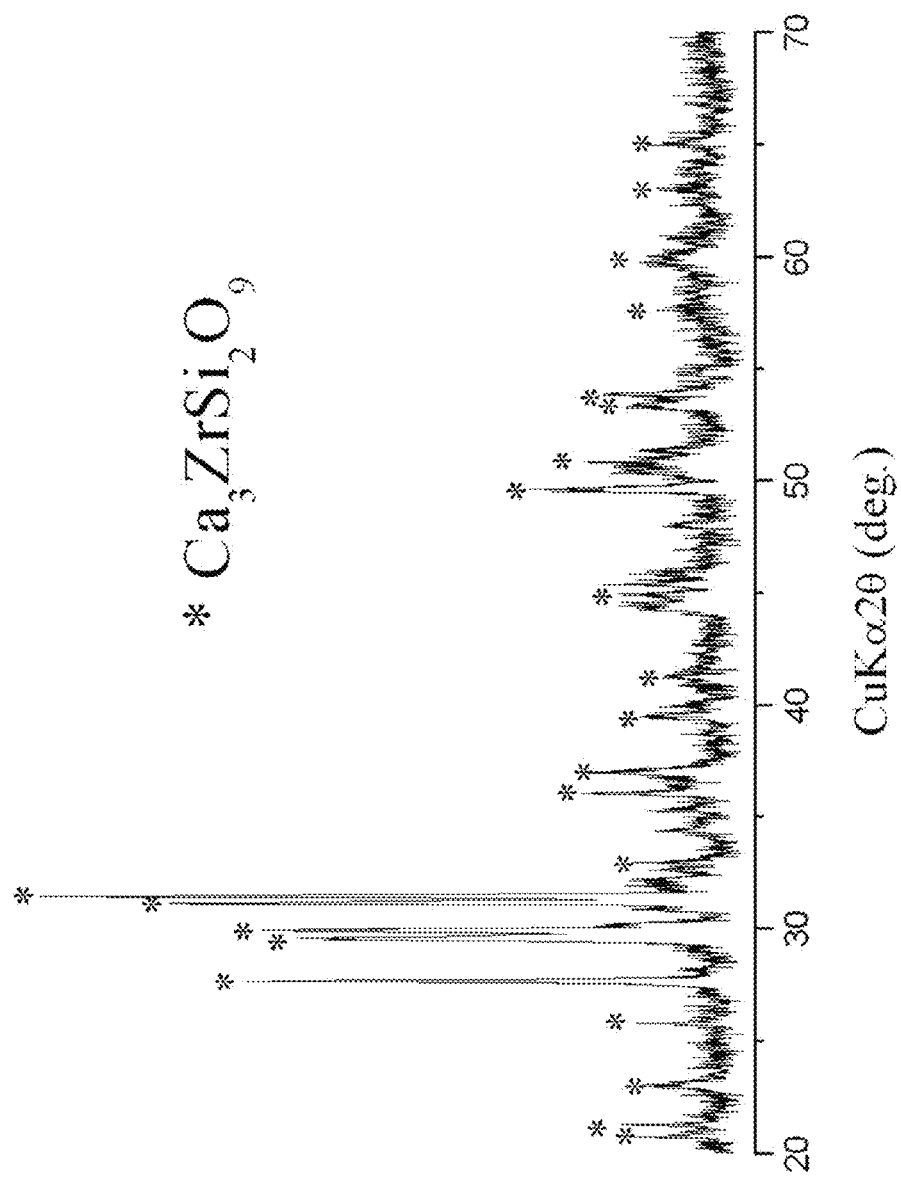
FIG. 2 is an XRD analysis of calcium zirconium silicate ceramic when pressed into a disc, highlighting the peaks characteristic of the ceramic.
Figure 3:
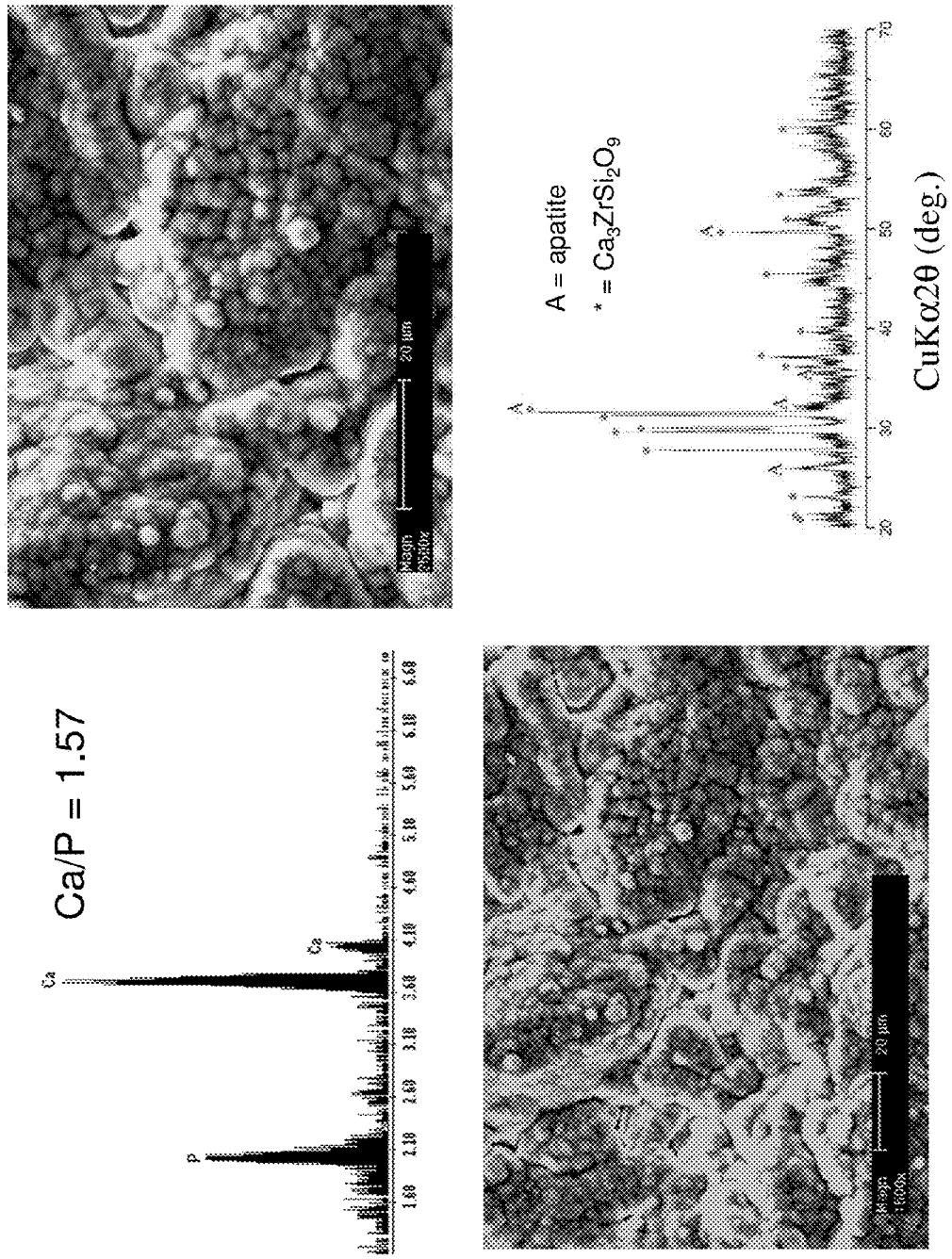
FIG. 3 shows SEM photographs of apatite formation on the calcium zirconium silicate of the invention with accompanying XRD and EDS analyses.
Figure 4:
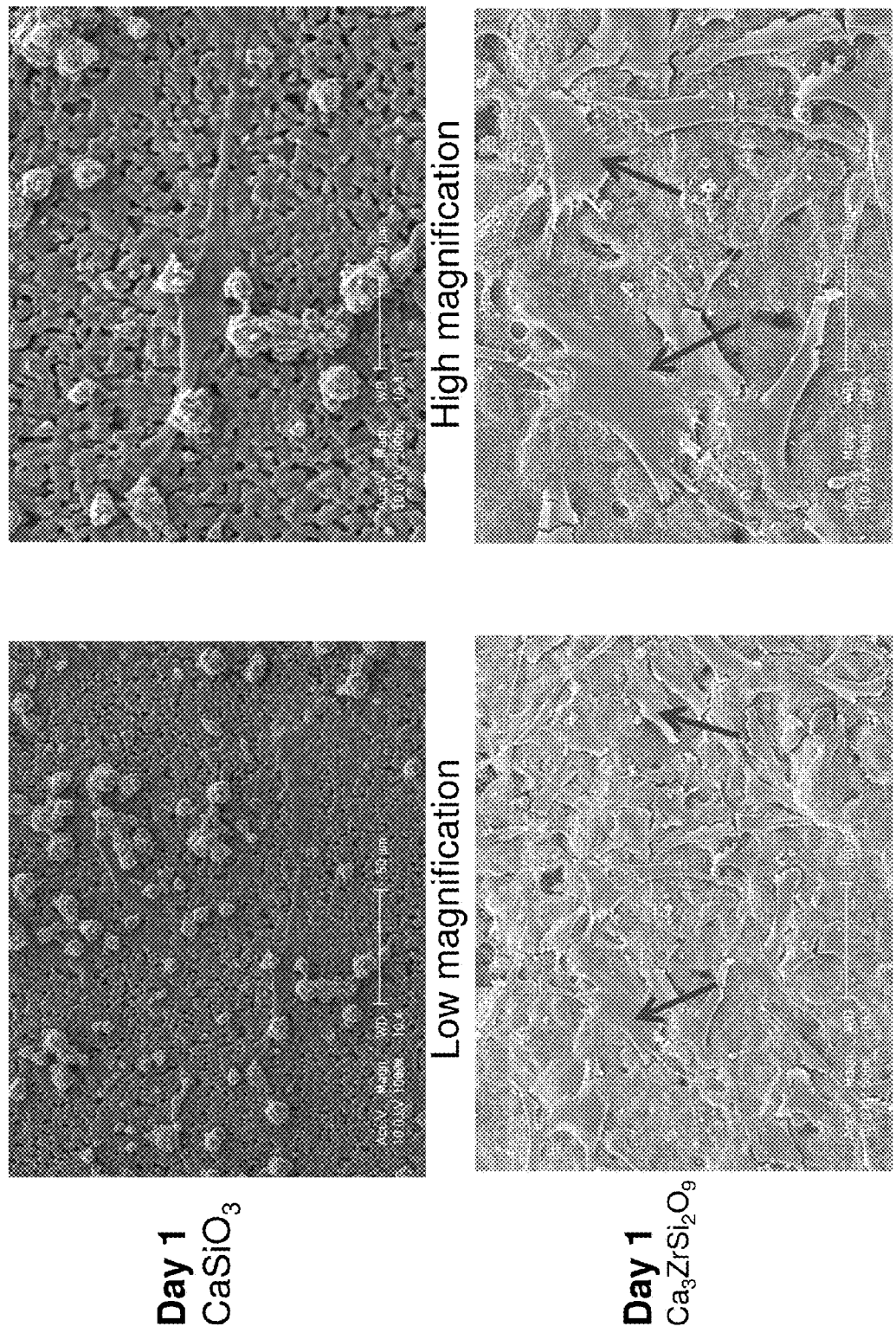
FIG. 4 shows SEM photographs at various magnifications of apatite formation on the calcium zirconium silicate of the invention compared to $CaSiO_3$.
Figure 5:
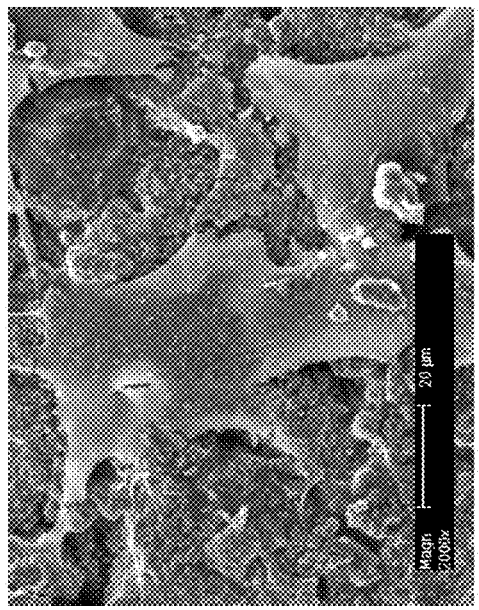
FIG. 5 shows SEM photographs at various magnifications of apatite formation on the calcium zirconium silicate of the invention.
Figure 5:
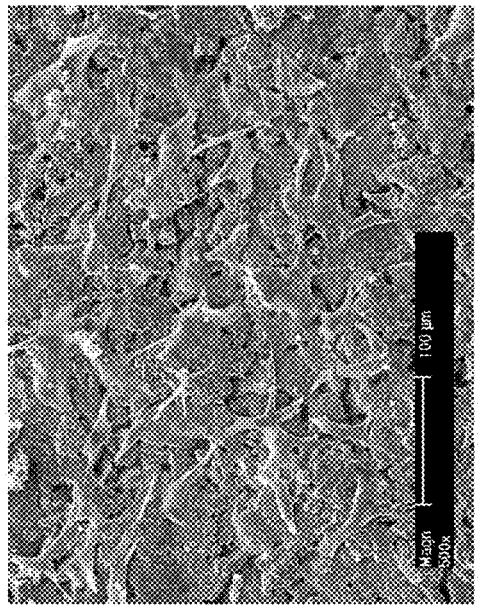
Figure 5:
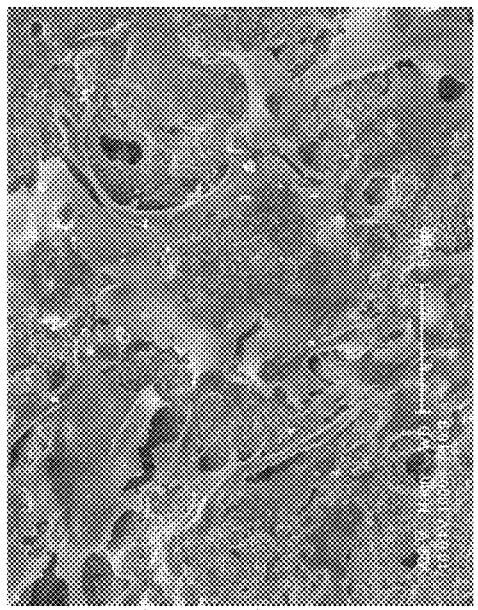
Figure 5:
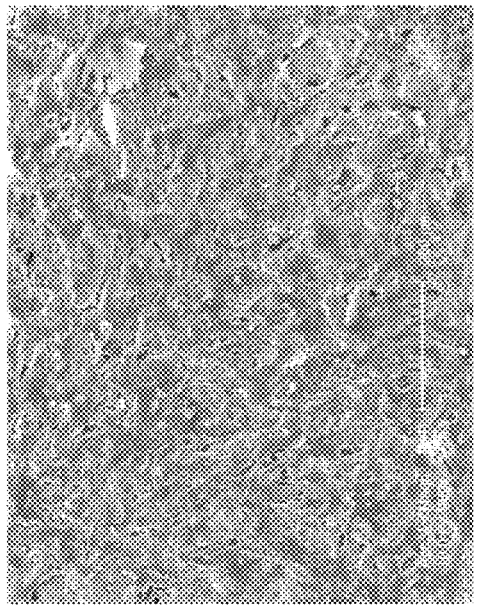
Figure 6:
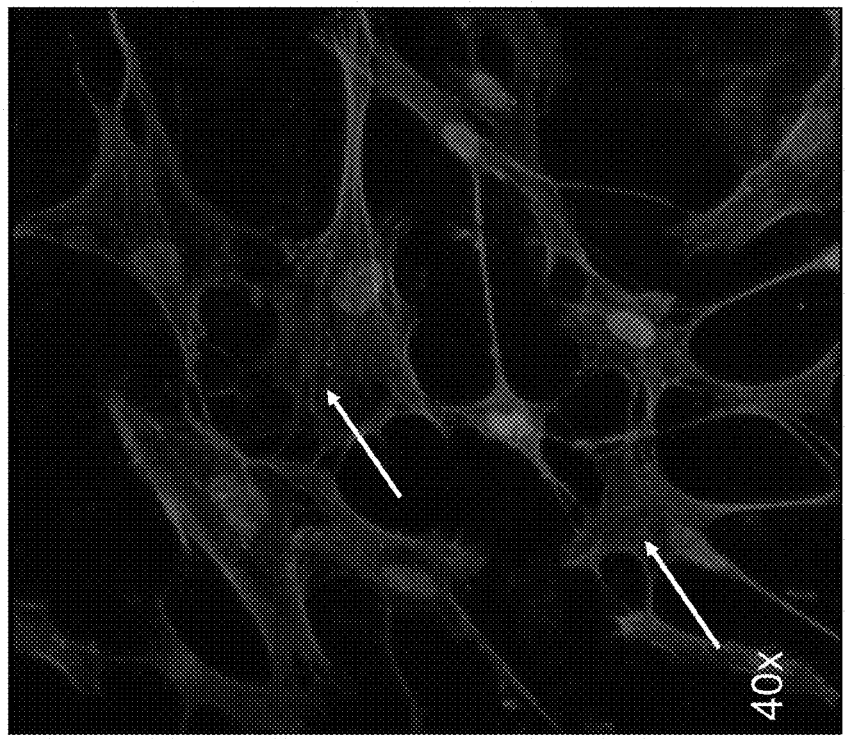
FIG. 6 shows cytoskeleton organisation of HOB on the calcium zirconium silicate of the invention compared to $CaSiO_3$.
Figure 6:
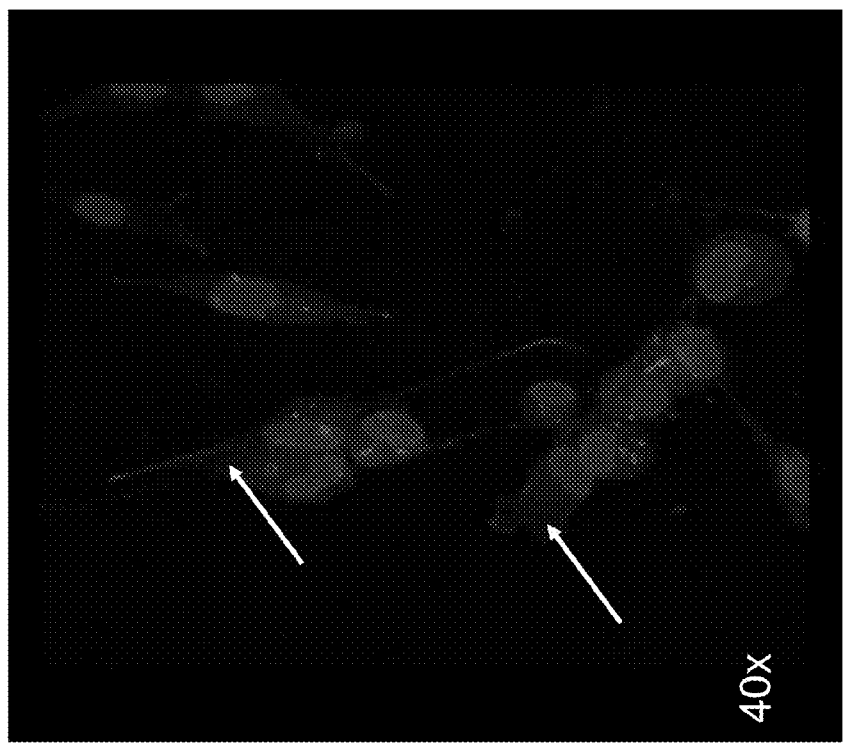

XRD analysis showed that pure $Ca_3ZrSi_2O_9$ ceramics were obtained (FIGS. 1 and 2). SEM micrographs showed that after soaking in SBF for 7 days, an obvious apatite layer formed on the surface of the ceramic disks (FIGS. 3 to 5 and 8), which was made up of micro- or nanocrystals. EDS analysis showed that the Ca/P ratio in the apatite layer was 1.57. The average surface roughness of $Ca_3ZrSi_2O_9$ disks (6.8±0.766 mm) was found to be significantly (p<0.05) higher than that of $CaSiO_3$ disks (2.3±0.926 mm).

Morphology of HOB

HOB attached onto $CaSiO_3$ ceramic did not show any significant spreading on days 1 and 3. In contrast, cells on $Ca_3ZrSi_2O_9$ attached and spread well with characteristic filapodialike processes. At day 7, HOB on $CaSiO_3$ showed some signs of spreading but was not comparable to $Ca_3ZrSi_2O_9$ where the cells were well spread, appeared more confluent, and formed a sheet-like layer.

Cytoskeletal Organization

On $Ca_3ZrSi_2O_9$, the rhodamine-phalloidin stained HOB revealed distinct and well defined stress fibers and actin containing microfilaments after 24 h of culturing. The cells on $CaSiO_3$ displayed weak and poorly structured actin filaments. Cell-cell contacts and numerous filapodia-like processes were observed on $Ca_3ZrSi_2O_9$, but were not evident on the $CaSiO_3$.

Cytotoxicity Test

The effect of ions released from $Ca_3ZrSi_2O_9$ and $CaSiO_3$ extracts (prepared at different concentrations) on HOB proliferation was evaluated at 1, 3 and 7 days. The tests showed that by day 7, the proliferation of HOB increased with increasing concentrations of extracts from $Ca_3ZrSi_2O_9$. It was significantly increased at higher extract concentration (100 and 200 mg/ml), compared to the blank control. However, with the $CaSiO_3$ extracts, the proliferation of HOB by day 7 was similar for all extract concentrations and did not show any significant differences compared to blank control. The ICP-AES analysis of the Si and Ca ions in $Ca_3ZrSi_2O_9$ and $CaSiO_3$ extracts also showed significant differences (Table 1).

Proliferation of HOB on Ceramic Disks

Figure 7:
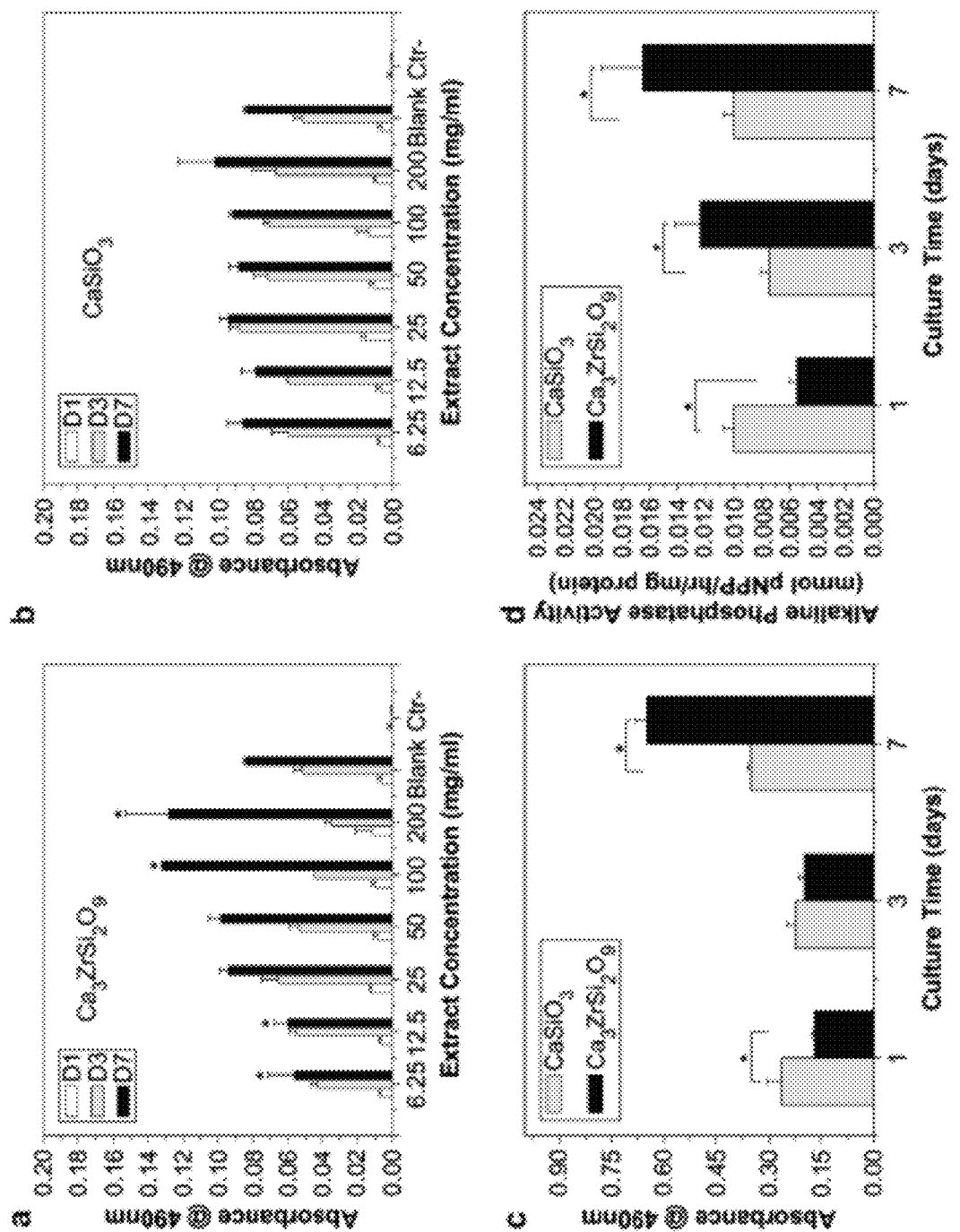
FIG. 7 shows (a) the effect of calcium zirconium silicate material of the invention and (b) $CaSiO_3$ extracts with different extract concentrations on HOB proliferation. The experimental group compared with the blank control group after 7 days of culture, $p<0.05$. Blank: blank control; Ctr−: negative control. (c) Proliferation of HOB and (d) alkaline phosphatase activity on $CaSiO_3$ and $Ca_3ZrSi_2O_9$ ceramics at day 1, 3 and 7. $Ca_3ZrSi_2O_9$ compared with $CaSiO_3$ after 1, 3 and 7 days of culture, $p<0.05$.
Figure 8:
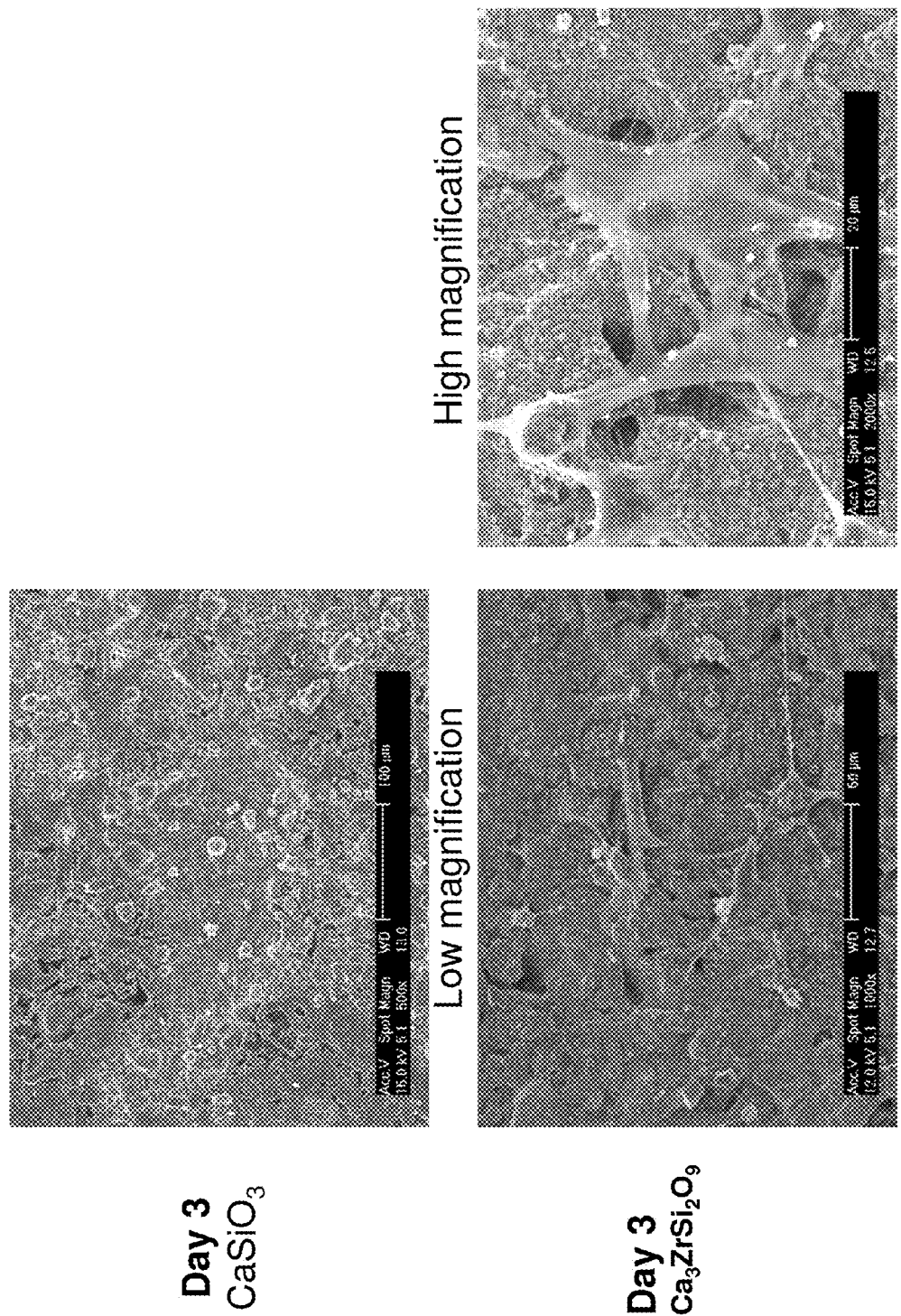
FIG. 8 shows further SEM photographs at various magnifications of apatite formation on the calcium zirconium silicate of the invention compared to $CaSiO_3$.

MTS assay demonstrated that on $CaSiO_3$, a significant (p<0.05) increase in HOB proliferation was found at day 1, compared to $Ca_3ZrSi_2O_9$ (FIG. 7B), while a similar trend was observed on day 3 but was not significant. However, by day 7 significant increase (p<0.05) in the proliferation of HOB cultured on $Ca_3ZrSi_2O_9$ was found compared to those cultured on $CaSiO_3$.

Differentiation of Hob on Ceramic Disks

ALP activity demonstrated that both ceramics supported HOB differentiation. On day 1, ALP activity was higher in HOB on $CaSiO_3$ compared to $Ca_3ZrSi_2O_9$. However, as time progressed in culture ALP activity increased in HOB on $Ca_3ZrSi_2O_9$ and was significantly (p<0.05) higher compared to $CaSiO_3$ (FIG. 7C) at 3 and 7 days. The ICP-AES analysis indicated that the concentration of the ions (Ca and Si) released from $Ca_3ZrSi_2O_9$ ceramic and the pH values were lower compared to that for $CaSiO_3$ ceramic at all time points tested (Table 2B).

Response of Osteoclast on Ceramics

Figure 9:
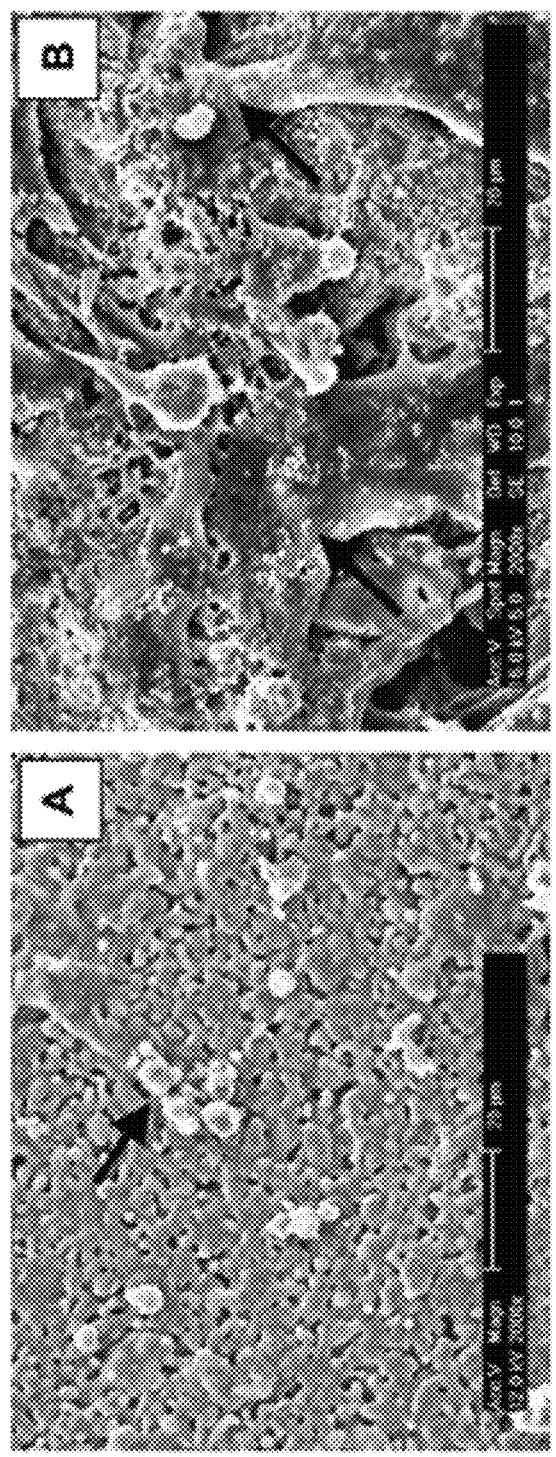
FIG. 9 shows SEM of human OC cultured for 21 days on ceramic disks (A) undifferentiated monocytes on $CaSiO_3$ (B) OC attachment on $Ca_3ZrSi_2O_9$.
Figure 10:
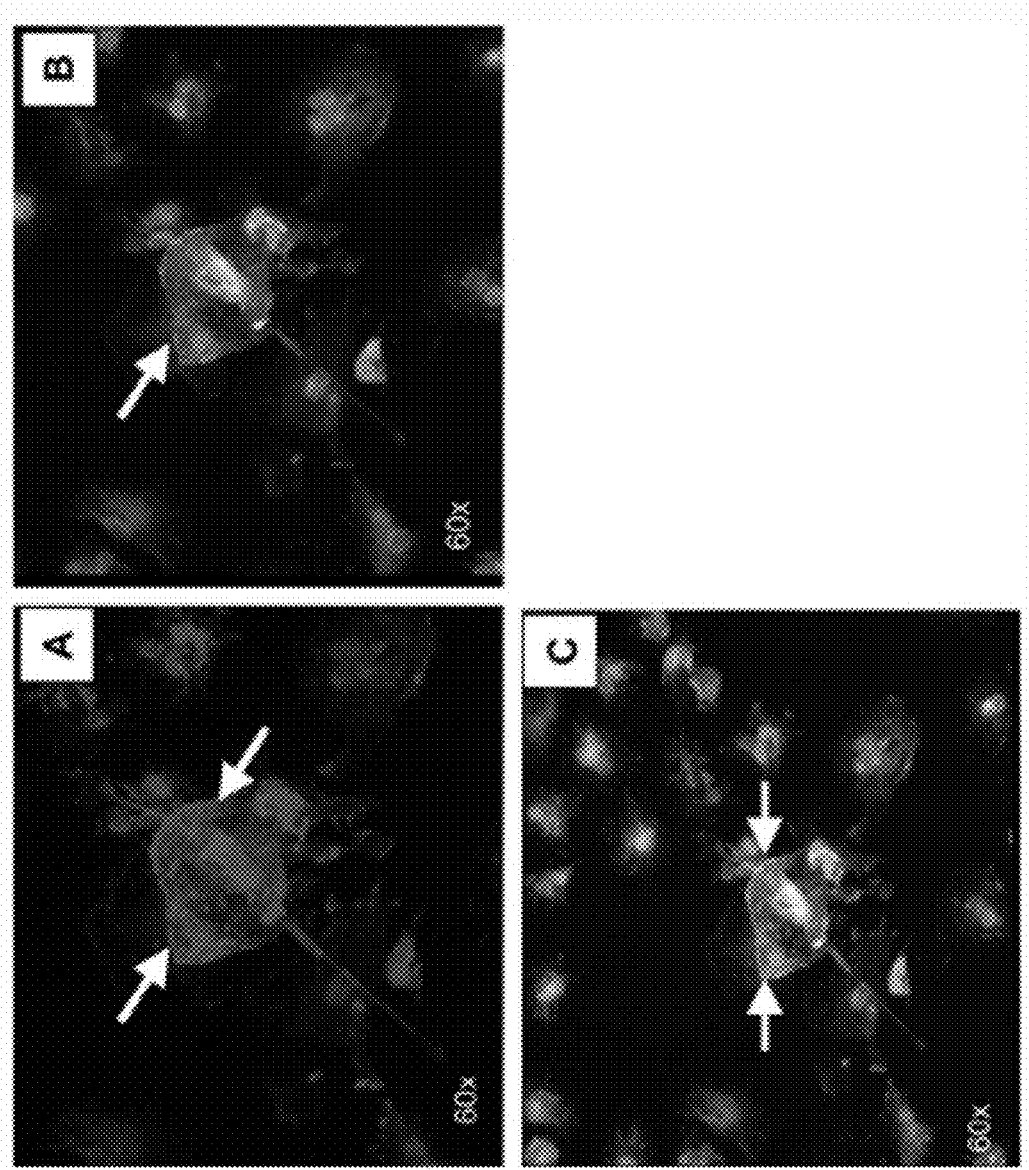
FIG. 10 shows fluorescence microscopy image of the actin ring and vitronectin of multinucleated cells on $Ca_3ZrSi_2O_9$ ceramic, after 21 days. (A) Actin ring (arrows); (B) vitronectin (arrows); and (C) co-localization of vitronectin and the surrounding actin ring.

The formation of OC was monitored on glass cover slips which were stained for TRAP and OC function was confirmed by observing pit formation on dentine (data not shown). SEM micrographs showed that the monocytes failed to differentiate and fuse to form any OC on $CaSiO_3$ (FIG. 9A), but on $Ca_3ZrSi_2O_9$, monocytes fused to form large well spread multinucleated giant cells with filapodialike processes and fine dorsal microvillai (FIG. 10B). The OC cultured on $Ca_3ZrSi_2O_9$ exhibited a thick band of f-actin with multi nuclei inside the actin ring (FIG. 10A). The avb3 subunit of the vitronectin receptor, essential for osteoclastic function, was also expressed (FIG. 10B).

Response of the Endothelial Cells

Figure 11:
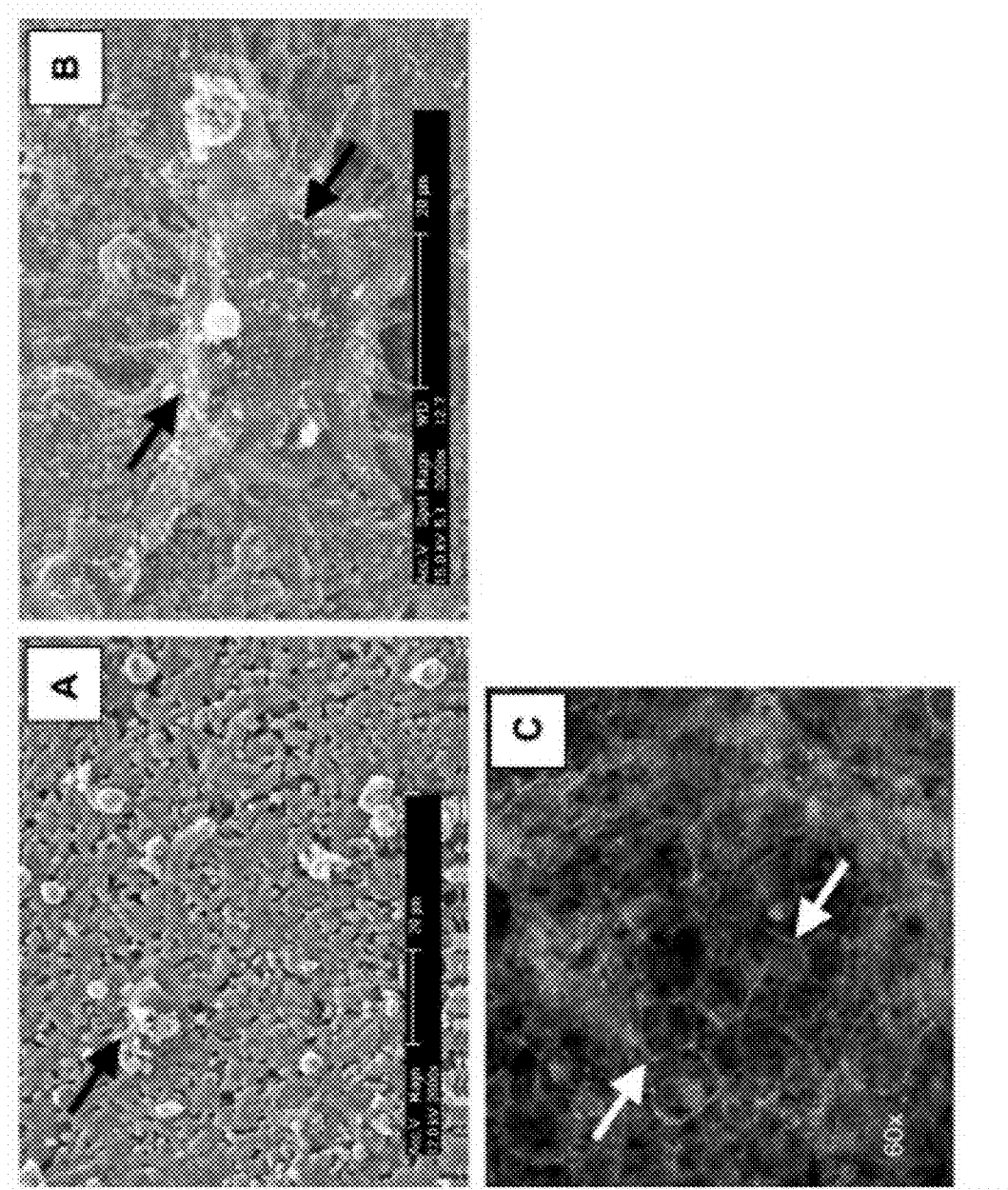
FIG. 11 shows SEM of endothelial cells attached on (A) $CaSiO_3$—no spreading of cells (arrow) (B) $Ca_3ZrSi_2O_9$ (C) ZO-1 expression of endothelial cells on $Ca_3ZrSi_2O_9$ (arrows).

Morphology of HMEC-1 on $Ca_3ZrSi_2O_9$ and $CaSiO_3$ was evaluated by SEM. After 3 days of culture the cells on $CaSiO_3$, were globular and did not spread (FIG. 11A). However, on $Ca_3ZrSi_2O_9$, HMEC-1 were firmly adherent and well spread (FIG. 11B) exhibiting numerous distinct pseudopodia. Immunofluorescence was used to detect the tight junction associated protein ZO-1 in the 7 days confluent HMEC-1 cultures on $Ca_3ZrSi_2O_9$ disks (FIG. 11C). This labelling shows expression of ZO-1 strongly associated with the plasma membrane of the cells and allows visualization of the cobblestone pattern of these cells present in normal conditions at confluence. HMEC-1 cells were cultured on both types of ceramics for 3 and 7 days to evaluate the mRNA levels of VE-Cadherin. $CaSiO_3$ expressed low levels of VE-Cadherin, compared to a significant (p<0.05) up-regulation at both 3 and 7 days, on $Ca_3ZrSi_2O_9$.

In summary, scaffolds of calcium zirconium silicate were successfully prepared having appropriate pore size and interconnectivity for bone-simulation applications. The biocompatible material of the invention exhibits an improved dissolution profile and pH compared to $CaSiO_3$, supports bone formation (shown by attachment and proliferation of osteoblasts) and supports vascularisation (shown by attachment of endothelial cells).

Although the invention has been described with reference to specific examples, it will be appreciated by those skilled in the art that the invention may be embodied in many other forms. In particular features of any one of the various described examples may be provided in any combination in any of the other described examples.

What is claimed is:

1. A biocompatible ceramic material comprising Baghdadite, wherein
    said Baghdadite is a medical grade or an implant grade material, wherein said material is in the form of a sintered ceramic,
    wherein said Baghdadite comprises a transmission X-ray diffraction pattern having the following diffraction angles 2θ:

lines of strong intensity: 31.385; 31.075 and 29.940 degrees, and lines of medium intensity: 27.662; 36.045 and 36.997 degrees.

2. The biocompatible ceramic material of claim 1 wherein said Baghdadite forms a hydroxyapatite layer upon exposure to bodily fluids.

3. The biocompatible ceramic material of claim 1 comprising a porosity of between about 10% to about 80%.

4. The biocompatible ceramic material of claim 1 wherein the pore size is between about 20 microns to about 500 microns.

5. The biocompatible ceramic material of claim 1 wherein the compressive strength is between 1.8 MPa to 5.1 MPa.

6. The biocompatible ceramic material of claim 1 having a network of pores sufficient to permit tissue and vascular in-growth and cell attachment when the material is employed as an implant or prosthesis.

7. An implantable medical device comprising a biocompatible ceramic material comprising Baghdadite, wherein said material is in the form of a sintered ceramic,
wherein said Baghdadite comprises a transmission X-ray diffraction pattern having the following diffraction angles 2θ:
lines of strong intensity: 31.385; 31.075 and 29.940 degrees, and lines of medium intensity: 27.662; 36.045 and 36.997 degrees.

8. The implantable medical device of claim 7 formed into a device chosen from: a 3D implantable scaffold, an orthopaedic implant for reconstructive surgery, a dental implant/prostheses, a spine implant, implants for craniofacial reconstruction and alveolar ridge augmentation, for cartilage regeneration, an osteochondral defect implant, a strut, a stent and a stent-graft.

9. The implantable medical device of claim 7 wherein said medical device is substantially biodegradable.

10. The implantable medical device of claim 7 comprising a porosity of between about 10 to about 80%.

11. The implantable medical device of claim 10 wherein the pore size is between about 20 to about 500 micron.

12. The implantable medical device of claim 7 wherein the compressive strength of the medical device is between 1.8 to 5.1 MPa.

13. The implantable medical device of claim 7 coated with at least one resorbable polymer material selected from polyglycolides, polydioxanones, polyhydroxyalkanoates, polylactides, alginates, collagens, chitosans, polyalkylene oxalate, polyanhydrides, poly(glycolide-co-trimethylene carbonate), polyesteramides, and polydepsipeptides.

14. The implantable medical device of claim 7 coated with at least one healing promoter selected from thrombosis inhibitors, fibrinolytic agents, vasodilator substances, anti-inflammatory agents, cell proliferation inhibitors, and inhibitors of matrix elaboration or expression.

15. The implantable medical device of claim 7 having a network of pores sufficient to permit tissue and vascular in-growth and cell attachment when the material is employed as an implant or prosthesis.

16. A bone implant comprising Baghdadite, wherein
said Baghdadite is a medical grade or an implant grade material, wherein said material is in the form of a sintered ceramic,
wherein said Baghdadite comprises a transmission X-ray diffraction pattern having the following diffraction angles 2θ:
lines of strong intensity: 31.385; 31.075 and 29.940 degrees, and lines of medium intensity: 27.662; 36.045 and 36.997 degrees.

17. A tooth filling implant comprising Baghdadite, wherein
said Baghdadite is a medical grade or an implant grade material, wherein said material is in the form of a sintered ceramic,
wherein said Baghdadite comprises a transmission X-ray diffraction pattern having the following diffraction angles 2θ:
lines of strong intensity: 31.385; 31.075 and 29.940 degrees, and lines of medium intensity: 27.662; 36.045 and 36.997 degrees.

18. A biocement comprising Baghdadite, wherein
said Baghdadite is a medical grade or an implant grade material, wherein said material is in the form of a sintered ceramic,
wherein said Baghdadite comprises a transmission X-ray diffraction pattern having the following diffraction angles 2θ:
lines of strong intensity: 31.385; 31.075 and 29.940 degrees, and lines of medium intensity: 27.662; 36.045 and 36.997 degrees.

19. A composite biocompatible material comprising Baghdadite, wherein
said Baghdadite is a medical grade or an implant grade material, wherein said material is in the form of a sintered ceramic,
wherein said Baghdadite comprises a transmission X-ray diffraction pattern having the following diffraction angles 2θ:
lines of strong intensity: 31.385; 31.075 and 29.940 degrees, and lines of medium intensity: 27.662; 36.045 and 36.997 degrees.

20. An implantable drug delivery device comprising calcium zirconium silicate, wherein
said calcium zirconium silicate is a medical grade or an implant grade material, wherein said material is in the form of a sintered ceramic,
wherein said calcium zirconium silicate comprises a transmission X-ray diffraction pattern having the following diffraction angles 2θ:
lines of strong intensity: 31.385; 31.075 and 29.940 degrees, and lines of medium intensity: 27.662; 36.045 and 36.997 degrees.

21. A kit for regenerating or resurfacing tissue, comprising Baghdadite and a therapeutic agent which stimulates and accelerates tissue regeneration, wherein
said Baghdadite is a medical grade or an implant grade material, wherein said material is in the form of a sintered ceramic,
wherein said Baghdadite comprises a transmission X-ray diffraction pattern having the following diffraction angles 2θ:
lines of strong intensity: 31.385; 31.075 and 29.940 degrees, and lines of medium intensity: 27.662; 36.045 and 36.997 degrees.

* * * * *